(12) United States Patent
Sham et al.

(10) Patent No.: US 11,471,061 B2
(45) Date of Patent: *Oct. 18, 2022

(54) APPARATUS AND METHOD FOR INTRAVASCULAR MEASUREMENTS

(71) Applicant: ZURICH MEDICAL CORPORATION, Plymouth, MN (US)

(72) Inventors: Kin-Joe Sham, Blaine, MN (US); James V. Donadio, III, Victoria, MN (US); Charles C. H. Chan, Minneapolis, MN (US); Paul Michael McSherry, Woodbury, MN (US); Paul J. Gam, Arden Hills, MN (US)

(73) Assignee: ZURICH MEDICAL CORPORATION, Plymouth, MN (US)

( * ) Notice: Subject to any disclaimer, the term of this patent is extended or adjusted under 35 U.S.C. 154(b) by 355 days.

This patent is subject to a terminal disclaimer.

(21) Appl. No.: 16/946,290

(22) Filed: Jun. 15, 2020

(65) Prior Publication Data

US 2020/0305728 A1 Oct. 1, 2020

Related U.S. Application Data

(63) Continuation of application No. 14/321,776, filed on Jul. 1, 2014, now Pat. No. 10,702,170.
(Continued)

(51) Int. Cl.
*A61B 5/0215* (2006.01)
*A61B 5/00* (2006.01)
*A61B 5/02* (2006.01)

(52) U.S. Cl.
CPC ........ *A61B 5/0215* (2013.01); *A61B 5/02007* (2013.01); *A61B 5/742* (2013.01);
(Continued)

(58) Field of Classification Search
None
See application file for complete search history.

(56) References Cited

U.S. PATENT DOCUMENTS

| | | |
|---|---|---|
| 4,691,709 A | 9/1987 | Cohen |
| 4,777,951 A | 10/1988 | Cribier et al. |

(Continued)

FOREIGN PATENT DOCUMENTS

| | | |
|---|---|---|
| CA | 2852174 A1 | 3/2013 |
| CN | 102202562 A | 9/2011 |

(Continued)

OTHER PUBLICATIONS

US 8,180,431 B2, 05/2012, Altmann et al. (withdrawn)
(Continued)

*Primary Examiner* — Michael R Bloch
(74) *Attorney, Agent, or Firm* — Carter, DeLuca & Farrell LLP

(57) ABSTRACT

Intravascular diagnosis apparatus and methods are disclosed. In one aspect of the disclosed technology, a intravascular diagnosis apparatus includes a monitoring guidewire and a display unit. The monitoring guidewire includes a core wire and a sensor disposed in a distal region of the core wire. The display unit includes a processor and a display screen, and is capable of receiving communication from the monitoring guidewire. The display unit is configured to perform computations using the processor based on communications received from the monitoring guidewire and is configured to display information on the display screen based on the computations. The display unit can be configured to be disposed after a predetermined number of uses or after a predetermined duration of use.

18 Claims, 10 Drawing Sheets

Related U.S. Application Data

(60) Provisional application No. 61/985,858, filed on Apr. 29, 2014, provisional application No. 61/841,517, filed on Jul. 1, 2013.

(52) U.S. Cl.
CPC ..... *A61B 5/7475* (2013.01); *A61B 2560/0204* (2013.01); *A61B 2560/028* (2013.01); *A61B 2560/0431* (2013.01)

(56) References Cited

U.S. PATENT DOCUMENTS

| | | | |
|---|---|---|---|
| 4,867,173 A | 9/1989 | Leoni | |
| 4,884,579 A | 12/1989 | Engelson | |
| 4,901,731 A | 2/1990 | Millar | |
| 4,928,693 A | 5/1990 | Goodin et al. | |
| 4,936,310 A | 6/1990 | Engstrom et al. | |
| 4,941,473 A | 7/1990 | Tenerz et al. | |
| 4,953,553 A | 9/1990 | Tremulis | |
| 5,040,543 A | 8/1991 | Badera et al. | |
| 5,063,935 A | 11/1991 | Gambale | |
| 5,065,769 A | 11/1991 | de Toledo | |
| 5,113,868 A | 5/1992 | Wise et al. | |
| 5,163,445 A | 11/1992 | Christian et al. | |
| 5,178,153 A | 1/1993 | Einzig | |
| 5,226,421 A | 7/1993 | Frisbie et al. | |
| 5,226,423 A | 7/1993 | Tenerz et al. | |
| 5,313,957 A * | 5/1994 | Little | G01L 9/0076 600/561 |
| 5,358,409 A | 10/1994 | Obara | |
| 5,412,994 A | 5/1995 | Cook et al. | |
| 5,413,508 A | 5/1995 | Obara | |
| 5,509,411 A | 4/1996 | Littmann et al. | |
| 5,517,989 A | 5/1996 | Frisbie et al. | |
| 5,549,109 A | 8/1996 | Samson et al. | |
| 5,668,320 A | 9/1997 | Cowan | |
| RE35,648 E | 11/1997 | Tenerz et al. | |
| 5,685,322 A | 11/1997 | Sung et al. | |
| 5,690,120 A | 11/1997 | Jacobsen et al. | |
| 5,699,796 A | 12/1997 | Littmann et al. | |
| 5,715,827 A | 2/1998 | Corl et al. | |
| 5,779,631 A * | 7/1998 | Chance | A61B 5/6828 600/328 |
| 5,797,856 A | 8/1998 | Frisbie et al. | |
| 5,807,265 A | 9/1998 | Itoigawa et al. | |
| 5,873,835 A | 2/1999 | Hastings et al. | |
| 5,916,177 A | 6/1999 | Schwager | |
| 5,938,624 A | 8/1999 | Akerfeldt et al. | |
| 6,004,279 A | 12/1999 | Crowley et al. | |
| 6,017,319 A | 1/2000 | Jacobsen et al. | |
| 6,089,103 A | 7/2000 | Smith | |
| 6,106,476 A | 8/2000 | Corl et al. | |
| 6,112,598 A | 9/2000 | Tenerz et al. | |
| 6,142,958 A | 11/2000 | Hammarstrom et al. | |
| 6,162,182 A | 12/2000 | Cole | |
| 6,167,763 B1 | 1/2001 | Tenerz et al. | |
| 6,183,424 B1 | 2/2001 | Schwager | |
| 6,193,669 B1 | 2/2001 | Degany et al. | |
| 6,196,980 B1 | 3/2001 | Akerfeldt et al. | |
| 6,210,339 B1 | 4/2001 | Kiepen et al. | |
| 6,248,083 B1 | 6/2001 | Smith et al. | |
| 6,265,792 B1 | 7/2001 | Granchukoff | |
| 6,312,380 B1 | 11/2001 | Hoek et al. | |
| 6,336,906 B1 | 1/2002 | Hammarstroem et al. | |
| 6,343,514 B1 | 2/2002 | Smith | |
| 6,379,308 B1 | 4/2002 | Brockway et al. | |
| 6,409,677 B1 | 6/2002 | Tulkki | |
| 6,428,336 B1 | 8/2002 | Akerfeldt | |
| 6,440,088 B1 | 8/2002 | Jacobsen et al. | |
| 6,461,301 B2 | 10/2002 | Smith | |
| 6,471,656 B1 * | 10/2002 | Shalman | A61B 5/6851 600/561 |
| 6,565,514 B2 | 5/2003 | Svanerudh et al. | |
| 6,579,246 B2 | 6/2003 | Jacobsen et al. | |
| 6,615,067 B2 | 9/2003 | Hoek et al. | |
| 6,615,667 B2 | 9/2003 | Smith | |
| 6,672,172 B2 | 1/2004 | Tulkki et al. | |
| 6,767,327 B1 | 7/2004 | Corl et al. | |
| 6,779,257 B2 | 8/2004 | Kiepen et al. | |
| 6,908,442 B2 | 6/2005 | von Malmborg et al. | |
| 6,926,674 B2 | 8/2005 | Tenerz et al. | |
| 6,976,965 B2 | 12/2005 | Corl et al. | |
| 7,017,420 B2 | 3/2006 | Kalvesten et al. | |
| 7,018,346 B2 | 3/2006 | Griffin et al. | |
| 7,097,620 B2 | 8/2006 | Corl et al. | |
| 7,134,994 B2 | 11/2006 | Alpert et al. | |
| 7,263,894 B2 | 9/2007 | Tenerz | |
| RE39,863 E | 10/2007 | Smith | |
| 7,326,204 B2 | 2/2008 | Paul et al. | |
| 7,450,989 B2 | 11/2008 | Svanerudh | |
| RE40,608 E | 12/2008 | Glover et al. | |
| 7,628,763 B2 | 12/2009 | Noriega et al. | |
| 7,676,910 B2 | 3/2010 | Kiepen et al. | |
| 7,706,891 B2 | 4/2010 | Hastings et al. | |
| 7,711,413 B2 | 5/2010 | Feldman et al. | |
| 7,774,051 B2 | 8/2010 | Voth | |
| 7,775,992 B2 | 8/2010 | von Malmborg et al. | |
| 7,857,810 B2 | 12/2010 | Wang et al. | |
| 7,878,981 B2 * | 2/2011 | Strother | A61B 5/4041 607/145 |
| 7,878,984 B2 | 2/2011 | Jacobsen et al. | |
| 7,914,466 B2 | 3/2011 | Davis et al. | |
| 7,931,603 B2 | 4/2011 | Von Malmborg et al. | |
| 7,967,761 B2 | 6/2011 | Smith | |
| 7,967,762 B2 | 6/2011 | Corl et al. | |
| 7,988,633 B2 | 8/2011 | Hossack et al. | |
| 7,988,639 B2 | 8/2011 | Starks | |
| 7,998,089 B2 | 8/2011 | Smith | |
| 8,012,145 B2 | 9/2011 | Cawley | |
| 8,043,312 B2 | 10/2011 | Noriega et al. | |
| 8,052,683 B2 | 11/2011 | Podmore et al. | |
| 8,075,490 B2 | 12/2011 | Lofgren et al. | |
| 8,105,246 B2 | 1/2012 | Voeller et al. | |
| 8,162,856 B2 | 4/2012 | Williams et al. | |
| 8,162,934 B2 | 4/2012 | Potter | |
| 8,174,395 B2 | 5/2012 | Samuelsson et al. | |
| 8,182,466 B2 | 5/2012 | Stehr et al. | |
| 8,216,151 B2 | 7/2012 | Smith | |
| 8,229,545 B2 | 7/2012 | Afonso | |
| 8,231,537 B2 | 7/2012 | Ahmed et al. | |
| 8,277,386 B2 | 10/2012 | Ahmed et al. | |
| 8,317,715 B2 | 11/2012 | Belleville et al. | |
| 8,340,766 B2 | 12/2012 | Ryu et al. | |
| 8,343,076 B2 | 1/2013 | Sela et al. | |
| 8,376,991 B2 | 2/2013 | Kauphusman et al. | |
| 8,382,689 B2 | 2/2013 | Sliwa et al. | |
| 8,391,956 B2 | 3/2013 | Zellers et al. | |
| 8,403,868 B2 | 3/2013 | Von Malmborg et al. | |
| 8,414,568 B2 | 4/2013 | Harlan | |
| 8,419,647 B2 | 4/2013 | Corl et al. | |
| 8,437,832 B2 | 5/2013 | Govari et al. | |
| 8,468,919 B2 | 6/2013 | Christian et al. | |
| 8,480,636 B2 | 7/2013 | Khieu et al. | |
| 8,485,985 B2 | 7/2013 | Manstrom et al. | |
| 8,551,020 B2 | 10/2013 | Chen et al. | |
| 8,551,021 B2 | 10/2013 | Voeller et al. | |
| 8,556,914 B2 | 10/2013 | Vrba | |
| 8,641,633 B2 | 2/2014 | Smith | |
| 8,657,789 B2 | 2/2014 | Guo et al. | |
| 8,684,962 B2 | 4/2014 | Kirschenman et al. | |
| 8,684,999 B2 | 4/2014 | Tegg et al. | |
| 8,696,584 B2 | 4/2014 | Kassab | |
| 8,702,613 B2 | 4/2014 | Kassab | |
| 8,734,440 B2 | 5/2014 | Wu | |
| 8,734,699 B2 | 5/2014 | Heideman et al. | |
| 8,755,860 B2 | 6/2014 | Paul et al. | |
| 8,758,333 B2 | 6/2014 | Harlan | |
| 8,764,683 B2 | 7/2014 | Meller et al. | |
| 8,777,929 B2 | 7/2014 | Schneider et al. | |
| 8,795,254 B2 | 8/2014 | Layman et al. | |
| 8,818,485 B2 | 8/2014 | Govari et al. | |
| 8,858,591 B2 | 10/2014 | Preinitz et al. | |
| 8,915,865 B2 | 12/2014 | Jacobsen et al. | |

(56) References Cited

U.S. PATENT DOCUMENTS

| | | | |
|---|---|---|---|
| 8,936,559 B2 | 1/2015 | Strommer et al. | |
| 8,979,837 B2 | 3/2015 | de la Rama et al. | |
| 8,989,849 B2 | 3/2015 | Milner et al. | |
| 8,998,826 B2 | 4/2015 | Hauck et al. | |
| 9,301,810 B2 | 4/2016 | Amiri et al. | |
| 9,326,756 B2 | 5/2016 | Stangenes et al. | |
| 2002/0072880 A1* | 6/2002 | Svanerudh | A61B 5/0215 702/189 |
| 2003/0023190 A1 | 1/2003 | Cox | |
| 2003/0032886 A1 | 2/2003 | Dgany et al. | |
| 2003/0069522 A1 | 4/2003 | Jacobsen et al. | |
| 2003/0216621 A1* | 11/2003 | Alpert | A61B 8/12 600/300 |
| 2004/0225232 A1 | 11/2004 | Malmborg et al. | |
| 2005/0096566 A1 | 5/2005 | Arnott | |
| 2006/0052700 A1 | 3/2006 | Svanerudh | |
| 2006/0074442 A1 | 4/2006 | Noriega et al. | |
| 2006/0135864 A1* | 6/2006 | Westerlund | A61B 3/16 600/587 |
| 2006/0211932 A1* | 9/2006 | Al-Ali | A61B 5/1455 600/326 |
| 2007/0010762 A1 | 1/2007 | Ressemann et al. | |
| 2007/0078352 A1 | 4/2007 | Pijls | |
| 2007/0185485 A1 | 8/2007 | Hauck et al. | |
| 2007/0255144 A1 | 11/2007 | Tulkki et al. | |
| 2007/0255145 A1 | 11/2007 | Smith et al. | |
| 2007/0270741 A1 | 11/2007 | Hassett et al. | |
| 2007/0299403 A1 | 12/2007 | Crowe et al. | |
| 2007/0299424 A1 | 12/2007 | Cumming et al. | |
| 2007/0299436 A1 | 12/2007 | Podmore et al. | |
| 2007/0299438 A1 | 12/2007 | Holzbaur et al. | |
| 2008/0091193 A1 | 4/2008 | Kauphusman et al. | |
| 2008/0140101 A1 | 6/2008 | Carley et al. | |
| 2008/0200773 A1 | 8/2008 | Pop | |
| 2008/0221438 A1 | 9/2008 | Chen et al. | |
| 2008/0221601 A1 | 9/2008 | Huynh et al. | |
| 2008/0262474 A1 | 10/2008 | Northrop | |
| 2009/0036832 A1 | 2/2009 | Skujins et al. | |
| 2009/0171345 A1 | 7/2009 | Miller et al. | |
| 2009/0177119 A1 | 7/2009 | Heidner et al. | |
| 2010/0125197 A1 | 5/2010 | Fishel | |
| 2010/0137736 A1 | 6/2010 | Addington et al. | |
| 2010/0228112 A1 | 9/2010 | Von Malmborg | |
| 2010/0234698 A1* | 9/2010 | Manstrom | A61B 5/02158 600/478 |
| 2010/0268038 A1* | 10/2010 | Smith | A61B 5/0215 600/300 |
| 2010/0305458 A1 | 12/2010 | Pfeiffer et al. | |
| 2010/0318000 A1 | 12/2010 | Von Malmborg et al. | |
| 2011/0004198 A1 | 1/2011 | Hoch | |
| 2011/0009694 A1* | 1/2011 | Schultz | A61B 1/0008 600/109 |
| 2011/0054487 A1 | 3/2011 | Farnan | |
| 2011/0152721 A1 | 6/2011 | Sela et al. | |
| 2011/0160680 A1 | 6/2011 | Cage et al. | |
| 2011/0160832 A1 | 6/2011 | Cohen | |
| 2011/0178413 A1* | 7/2011 | Schmitt | A61B 5/0215 600/478 |
| 2012/0172731 A1 | 7/2012 | Smith | |
| 2012/0278008 A1 | 11/2012 | Davies et al. | |
| 2012/0289808 A1* | 11/2012 | Hubinette | A61B 5/0002 600/381 |
| 2013/0046190 A1 | 2/2013 | Davies | |
| 2013/0046202 A1 | 2/2013 | Tsunezumi et al. | |
| 2013/0076157 A1* | 3/2013 | Stein | A61B 5/103 307/116 |
| 2013/0102927 A1 | 4/2013 | Hilmersson | |
| 2013/0116579 A1 | 5/2013 | Svanerudh | |
| 2013/0131523 A1 | 5/2013 | Suchecki et al. | |
| 2013/0131663 A1 | 5/2013 | Govari et al. | |
| 2013/0172782 A1 | 7/2013 | Hilmersson | |
| 2013/0190633 A1 | 7/2013 | Dorando et al. | |
| 2013/0218032 A1 | 8/2013 | Belleville | |
| 2013/0237864 A1 | 9/2013 | Mazar et al. | |
| 2013/0274618 A1 | 10/2013 | Hou et al. | |
| 2013/0296692 A1 | 11/2013 | Vanney et al. | |
| 2013/0296718 A1 | 11/2013 | Ranganathan et al. | |
| 2013/0296722 A1 | 11/2013 | Warnking et al. | |
| 2013/0317372 A1 | 11/2013 | Eberle et al. | |
| 2013/0324842 A1 | 12/2013 | Mittal et al. | |
| 2013/0338538 A1 | 12/2013 | Park et al. | |
| 2014/0005558 A1 | 1/2014 | Gregorich | |
| 2014/0039325 A1 | 2/2014 | Belleville | |
| 2014/0058275 A1 | 2/2014 | Gregorich et al. | |
| 2014/0058715 A1 | 2/2014 | Sharma et al. | |
| 2014/0066790 A1 | 3/2014 | Burkett et al. | |
| 2014/0066791 A1 | 3/2014 | Burkett | |
| 2014/0081244 A1 | 3/2014 | Voeller et al. | |
| 2014/0107624 A1 | 4/2014 | Belleville | |
| 2014/0180028 A1 | 6/2014 | Burkett | |
| 2014/0187979 A1 | 7/2014 | Burkett | |
| 2014/0187983 A1 | 7/2014 | Anderson | |
| 2014/0276109 A1 | 9/2014 | Gregorich | |
| 2014/0276117 A1 | 9/2014 | Burkett | |
| 2014/0276223 A1 | 9/2014 | Gustafsson | |
| 2014/0276226 A1 | 9/2014 | Meller et al. | |
| 2014/0336620 A1 | 11/2014 | Layman et al. | |
| 2015/0032027 A1 | 1/2015 | Lupton | |

FOREIGN PATENT DOCUMENTS

| | | |
|---|---|---|
| EP | 0879615 A1 | 11/1998 |
| EP | 1125548 A1 | 8/2001 |
| EP | 1310215 A1 | 5/2003 |
| EP | 0877574 B1 | 10/2003 |
| EP | 0973438 B1 | 11/2003 |
| EP | 1433429 A2 | 6/2004 |
| EP | 1076511 B1 | 8/2004 |
| EP | 1125548 B1 | 4/2005 |
| EP | 0968547 B1 | 8/2005 |
| EP | 1012912 B1 | 12/2005 |
| EP | 0907335 B1 | 9/2006 |
| EP | 1837638 A1 | 9/2007 |
| EP | 1849409 A1 | 10/2007 |
| EP | 1055392 B1 | 3/2008 |
| EP | 1922988 A1 | 5/2008 |
| EP | 2042091 A1 | 4/2009 |
| EP | 1608418 B1 | 7/2009 |
| SE | 523337 C2 | 4/2004 |
| WO | 2001021057 A2 | 3/2001 |
| WO | 2003022122 A2 | 3/2003 |
| WO | 2009020836 A1 | 2/2009 |
| WO | 2011110817 A2 | 9/2011 |
| WO | 2012000798 A1 | 1/2012 |
| WO | 2012041905 A1 | 4/2012 |
| WO | 2012061935 A1 | 5/2012 |
| WO | 2012091783 A1 | 7/2012 |
| WO | 2012173697 A1 | 12/2012 |
| WO | 2013028737 A1 | 2/2013 |
| WO | 2013092969 A2 | 6/2013 |
| WO | 2013164682 A1 | 11/2013 |
| WO | 2013169451 A1 | 11/2013 |
| WO | 2014005095 A1 | 1/2014 |
| WO | 2014025255 A1 | 2/2014 |
| WO | 2014043704 A1 | 3/2014 |
| WO | 2014105578 A1 | 7/2014 |
| WO | 2014140883 A1 | 9/2014 |
| WO | 2014149688 A1 | 9/2014 |

OTHER PUBLICATIONS

Notification of Transmittal of the International Search Report and the Written Opinion of the International Searching Authority, or the Declaration issued in corresponding application No. PCT/US2016/037389 dated Sep. 27, 2016.

B. Nudell, et al., "Fame II Good for FFR and PCI", Credit Suisse Securities Research & Analytics, Americas/United States, Equity Research, Medical Supplies & Devices, Aug. 28, 2012, pp. 1-9.

M. Weinstein, et al. "Cardiovascular Devices, Fame II: The Drumbeat of Data Supporting Broader FFR Use Continues", J.P. Morgan North America Equity Research, Aug. 28, 2012 pp. 1-6.

(56) References Cited

OTHER PUBLICATIONS

"PressureWire(TM) Certus(TM) with Agile Tip", St. Jude Medical, 2012, pp. 1-2.
S. Sen, et al., "Development and Validation of a New Adenosine-Independent Index of Stenosis Severity From Coronary Wave-Intensity Analysis", Journal of the American College of Cardiology, vol. 59, No. 15, Apr. 10, 2012, pp. 1392-1402.
R. Petraco et al., "Classification performance of instantaneous wave-free ratio (iFR) and fractional flow reserve in a clinical population of intermediate coronary stenoses: results of the ADVISE registry", EuroIntervention 2013; 9: 91-101.
De Bruyne et al, "Fractional Flow Reserve-Guided PCI versus Medical Therapy in Stable Coronary Disease", The New England Journal of Medicine, vol. 367, No. 11, Sep. 13, 2012, pp. 991-1001.
"St. Jude Medical executive: FAMI II trial's FFR products showing 'significant growth'", http://medcitynews.com/2012/01/fame-ii-trials-ffr-products-showing-significant-growth-st- . . . Jan. 19, 2012.
P. Tonino et al., "Fractional Flow Reserve versus Angiography for Guiding Percutaneous Coronary Intervention", The New England Journal of Medicine, vol. 360, No. 3, Jan. 15, 2009, pp. 213-224.
R. Petraco et al., "Hybrid iFR-FFR decision-making strategy: implications for enhancing universal adoption of physiology-guided coronary revascularisation", EuroIntervention 2013; 8:1157-1165.
Written Opinion of the International Searching Authority issued in corresponding application No. PCT/US14/45171dated Jan. 21, 2015.
PCT International Search Report issued in corresponding application No. PCT/US2014/045171 dated Jan. 21, 2015.
Volcano Announces Preliminary Results from the ADVISE II Study and Inclusion in the SYNTAX2 Trial During Hot Line Late Breaking Clinical Trial Sessions at EuroPCR 2013, PR Newswire—Thursday, May 23, 2013 (<http://m.yahoo.com/w/legobpengine/finance/news/volcano-announces-preliminary-results-advise-083000929.html?.intl=us&.lang=en-us>).
Instructions for use PrimeWire Presige(R) Plus, Pressure Guide Wire, Models: 9185/9185J-9300/9300J English, Volcano, Aug. 2012.
"Importance of FFR in Treatment of Coronary Artery Disease Confirmed by New PCI Guidelines", St. Jude Medical News Release, Dec. 16, 2009, pp. 1-3.
Instructions for Use for PressureWire(TM) Aeris (TM) Wireless FFR Measurement System, St. Jude Medical, Nov. 18, 2010. pp. 1-17.
Instructions for Use for PressureWire(TM) Receiver, St. Jude Medical, Oct. 18, 2010, pp. 1-15.
Quantien(TM) Integrated FFR Platform, St. Jude Medical, Jul. 10, 2013 (http://professional.sjm.com/products/vas/intravascular-diagnostics-imaging/ffr/quantien).
Quantien(TM) Integrated FFR Platform, Dicom Conformance Statement Model Quantien—Cardiology, Revision A, St. Jude Medical, 2012, pp. 1-29.
C. Berry et al., "VERIFY (VERification of Instantaneous Wave-Free Ratio and Fractional Flow Reserve for the Assessment of Coronary Artery Stenosis Severity in Every Practice)", Journal of the American College of Cardiology, vol. 16, No. 13, 2013, pp. 1421-1427.
"ADVISE Study Results Demonstrate the Instant Wave-Free Ratio (TM), a Vasodilate Free Measure of Stenosis Severity, is Comparable to FFR", Volcano Corporation and Imperial College London Support Study Presented During Late Breaking Clinical Trial Session at TCT Nov. 14, 2011.
Instructions for Use for "Combowire(R) Pressure/Flow Guide Wire Ref 9500 Series", Volcano Corporation, Revision Date: Feb. 2012, pp. 1-4.
Instructions for Use for "FloWire(R) Doppler Guide Wire REF 1400 Series—FloWire", Volcano Corporation, Revision Date Feb. 2012.
Instructions for use for "PrimeWire Prestige(R) Pressue Guide Wire", Models: 8185/8185J-8300/8300J, Volcano Corporation, Revision Date Nov. 2012.
Instructions for use for "PrimeWire Prestige(R) Plus Pressure Guide Wire", Models: 9185/9185J-9300/9300J, Volcano Corporation, Revision Date Aug. 2012.
Instructions for use for "Veratta(R) Pressue Guide Wire", Models: 10185/10185J-10300/10300J, Volcano Corporation, Revision Date Jan. 2014.
Investorplace, "Volcano, St. Jude: 2 hearts beat as one. The Companies dominate a potential $2 billion test market." Jan. 14, 2013 (http://money.msn.com/top-stocks/post.aspx?post=3bb89ca7-9959-4173-910e-eee3fc37a742).
J. Brosky, "Drug-free lesion assessment rivals fractional flow reserve", Medical Device Daily, EuroPCR May 29, 2013 (http://www.medicaldevicedaily.com/servlet/com.accumedia.web.Dispatcher?next=bioWorl . . . ).
Volcano Corporation S5/S5i (Chinese), www.dragonmedical.com, retrieved from internet Dec. 22, 2013.
"Wi-Box(TM) Cath Lab Installation and FAQ Dec. 2011", St. Jude Medical, 2011.
"FFR and PressureWire(TM) Certus", St. Jude Medical, p. 1-34, retrieved from internet Feb. 9, 2014.
"SJM PressureWire Certus IFU (2)", St. Jude Medical, pp. 4-13, www.sjm.com, retrieved from internet Jun. 29, 2013.
"SJM RadiAnalyzer IFU", 20645 IFU RANXpress ENG R03 2010-12.indd, St. Jude Medical, pp. 3-48; 2010.
"PressureWire(TM) Agile Tip Technology", St. Jude Medical, p. 1-15; 2012.
Partial European Search Report issued in corresponding U.S. Appl. No. 14/820,180 dated Jan. 10, 2017.
Extended European Search Report issued in corresponding application No. 14820180.9 dated Mar. 20, 2017.
Chinese First Office Action issued in corresponding application No. 201480002922.4 dated Dec. 12, 2017.
Australian Examination Report No. 1 for Australian Appln. No. AU 2014284381 dated Apr. 6, 2018 (3 pages).
Australian Examination Report No. 2 for Australian Appln. No. AU 2014284381 dated Dec. 7, 2018 (3 pages).
De Bruyne et al., "Coronary Flow Reserve Calculated From Pressure Measurements in Humans. Validation With Positron Emission Tomography," Circulation, Journal of the American Heart Association, Mar. 1994, vol. 89, No. 3, pp. 1013-1022.
Allie et al., "Pressure-Sensing Guidewire Analysis in RAS," Endovascular Today, Oct. 2004, pp. 14-26.
Examination Report issued by the Australian Patent Office dated Mar. 19, 2020 in corresponding Australian Patent Application No. 2016282495.
Communication issued by the European Patent Office dated May 20, 2020 in corresponding European Patent Application No. 14820180.9.
Office Action issued in corresponding Canadian application 2915252 dated Dec. 17, 2021 (6 pages).
Office Action issued in corresponding application CA 2,915,252 dated Mar. 15, 2021 (6 pages).

\* cited by examiner

APPARATUS AND METHOD FOR INTRAVASCULAR MEASUREMENTS

CROSS-REFERENCE TO RELATED APPLICATIONS

This application is a continuation of U.S. patent application Ser. No. 14/321,776, filed Jul. 1, 2014, which claims priority to U.S. Provisional Application No. 61/985,858, filed Apr. 29, 2014, and to U.S. Provisional Application No. 61/841,517, filed Jul. 1, 2013. The entire contents of each and every priority application are hereby incorporated by reference herein.

FIELD OF THE INVENTION

The disclosed technology relates to intravascular diagnosis. More particularly, the disclosed technology relates to diagnosing the severity of stenosis in the vasculature of a patient.

BACKGROUND

Reduced blood flow due to atherosclerotic occlusion of vessels is a major cause of vascular diseases. Pressure measurements in arterial vessels and particularly in coronary arteries prior to treatment have been used for lesion characterization and treatment selection. More specifically, pressure gradient across a lesion has been clinically used as an indicator for lesion severity. Measurements made during and after treatment allow one to assess therapy efficacy. Existing equipment for monitoring intravascular measurements have multiple, separate parts and bulky monitors. There is, accordingly, continuing interest in improved monitoring equipment.

SUMMARY

The disclosed technology relates to diagnosing the severity of stenoses in the vasculature of a patient.

In one aspect of the disclosed technology, an apparatus for intravascular diagnosis includes a monitoring guidewire having a core wire and a sensor disposed in a distal region of the core wire, and a portable display unit configured to be disposed after a predetermined number of uses or after a predetermined duration of use. The portable display unit can include a processor and a display screen, where the portable display unit is capable of receiving communication from the monitoring guidewire, is configured to perform computations using the processor based on communications received from the monitoring guidewire, and is configured to display information on the display screen based on the computations.

In one embodiment, the portable display unit includes one or more batteries configured to power the portable display unit. In one embodiment, the one or more batteries can be rechargeable by a power source of the portable display unit and/or a power source external to the portable display unit.

In one embodiment, the portable display unit further includes one or more batteries configured to power the portable display unit for a predetermined duration of use, such that the portable display unit can be configured to be disposed after the one or more batteries are depleted. In one embodiment, the one or more batteries are non-rechargeable. In one embodiment, the portable display unit can be configured to be inoperable after a one uses.

In one aspect of the disclosed technology, the monitoring guidewire can be configured to be disposed after a single use.

In one embodiment, the portable display unit and the monitoring guidewire can communicate wirelessly. In one embodiment, the portable display unit includes a connector configured to establish a communicative connection with the monitoring guidewire. In one embodiment, the connector is configured to establish a mechanical connection with the monitoring guidewire to control the guidewire within a vasculature. In one embodiment, a torquer is configured to engage the monitoring guidewire to control the guidewire within a vasculature.

In one embodiment, the monitoring guidewire includes a housing surrounding the sensor, and the housing can be laser etched to provide flexibility for the housing. In one embodiment, the monitoring guidewire includes a flexible coil surrounding the sensor, with the coil having a relaxed portion over the sensor.

In one aspect of the disclosed technology, the sensor is a pressure sensor and communication from the monitoring guidewire includes measurements from the pressure sensor. The processor of the portable display unit is capable of computing fractional flow reserve based on pressure measurements from only the pressure sensor in the distal region of the core wire.

In one embodiment, the fractional flow reserve is a push-forward fraction flow reserve ("FFR") computed as: $FFR=(P_{sensor}-P_{ra})/(P_{saved}-P_{ra})$, where:

$P_{saved}$ are moving means over time of recorded pressure measurements proximal to a first stenosis, $P_{sensor}$ are moving means over time of real time pressure measurements distal to the first stenosis, and $P_{ra}$ is a constant.

In one embodiment, $P_{saved}$ are moving means over time of recorded pressure measurements proximal to the first stenosis and proximal to a second stenosis. In one embodiment, $P_{sensor}$ are moving means over time of real time pressure measurements distal to the first stenosis and proximal to a second stenosis. In one embodiment, $P_{sensor}$ moving means over time of real time pressure measurements distal to the first stenosis and distal to the second stenosis.

In one embodiment, the fractional flow reserve is a pull-back fraction flow reserve computed as: $FFR=(P_{saved}-)/(P_{sensor}-P_{ra})$, where:

$P_{saved}$ are moving means over time of recorded pressure measurements distal to a first stenosis, $P_{sensor}$ are moving means over time of real time pressure measurements proximal to the first stenosis, and $P_{ra}$ is a constant.

In one embodiment, $P_{sensor}$ are moving means over time of real time pressure measurements proximal to the first stenosis and distal to a second stenosis. In one embodiment, $P_{saved}$ are moving means over time of recorded pressure measurements distal to the first stenosis and distal to a second stenosis. In one embodiment, $P_{sensor}$ are moving means over time of real time pressure measurements proximal to the first stenosis and proximal to the second stenosis.

In one embodiment, the portable display unit displays on the display screen the fractional flow reserve. In one embodiment, the portable display unit displays a graph of the pressure measurements.

In one embodiment, the portable display unit includes a communications port configured to receive communications that include pressure measurements.

In one embodiment, the fractional flow reserve is a pull-back fraction flow reserve computed as: $FFR=(P_{sensor}-P_{ra})/(P_{port}-P_{ra})$, where:

$P_{port}$ are moving means over time of real-time pressure measurements received at the communications port, $P_{sensor}$ are moving means over time of real-time pressure measurements from the pressure sensor disposed in the distal region of the core wire, and $P_{ra}$ is a constant.

In one embodiment, the portable display unit is configured with capability to compute fractional flow reserve in at least two ways: computing fractional flow reserve based on pressure measurements from only the pressure sensor disposed in the distal region of the core wire, and computing fractional flow reserve based on the pressure measurements from the pressure sensor and based on pressure measurements received at a communications port. In one embodiment, the portable display unit can be configured to automatically use one of the at least two ways of computing fractional flow reserve. In one embodiment, the portable display unit can be configured to automatically select one of the ways of computing fractional flow reserve when a condition is present and can be configured to automatically select another of the at least two ways of computing fractional flow reserve when the condition is absent. In one embodiment, the portable display unit can be configured to permit a user to manually select one of the at least two ways of computing fraction flow reserve.

In one aspect of the disclosed technology, an apparatus for intravascular diagnosis includes a monitoring guidewire having a core wire and a sensor disposed in a distal region of the core wire, and a handheld display unit configured to be disposed after a predetermined number of uses or after a predetermined duration of use. The handheld display unit can include a processor and a display screen, where the handheld display unit is capable of receiving communication from the monitoring guidewire, is configured to perform computations using the processor based on communications received from the monitoring guidewire, and is configured to display information on the display screen based on the computations. In one embodiment, the handheld display unit can be equal to or less than 30 cm×30 cm×30 cm in size.

In one aspect of the disclosed technology, an apparatus for intravascular diagnosis includes a monitoring guidewire having a core wire and a sensor disposed in a distal region of the core wire, and a portable display unit capable of receiving communication from the monitoring guidewire. The portable display unit includes a processor and display screen, and is configured to perform computations using the processor based on communications received from the monitoring guidewire and is configured to display information on the display screen based on the computations. The portable display unit has no capability of being turned off after the display screen is turned on, These aspects and embodiments of the disclosed technology are exemplary and do not limit the scope of the disclosed technology, which will be apparent from a reading of the following detailed description and the associated drawings.

DETAILED DESCRIPTION

The disclosed technology relates to diagnosing the severity of stenosis in the vasculature of a patient. The disclosed technology can be used as an adjunct to conventional angiographic procedures to provide important quantitative measurements of a blood vessel lumen.

Figure 1:
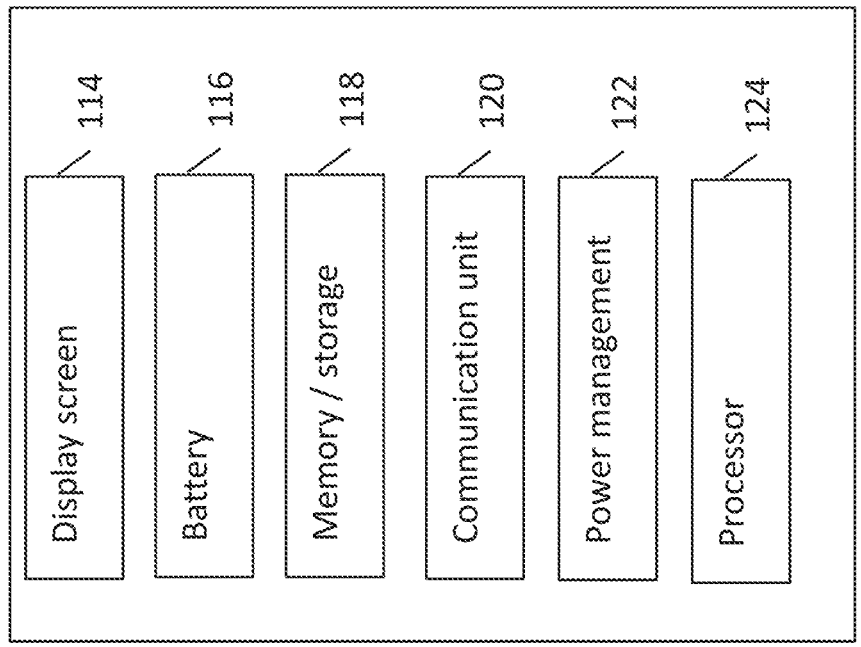
FIG. 1 is a block diagram of an exemplary intravascular diagnosis apparatus in accordance with the disclosed technology.
Figure 1:
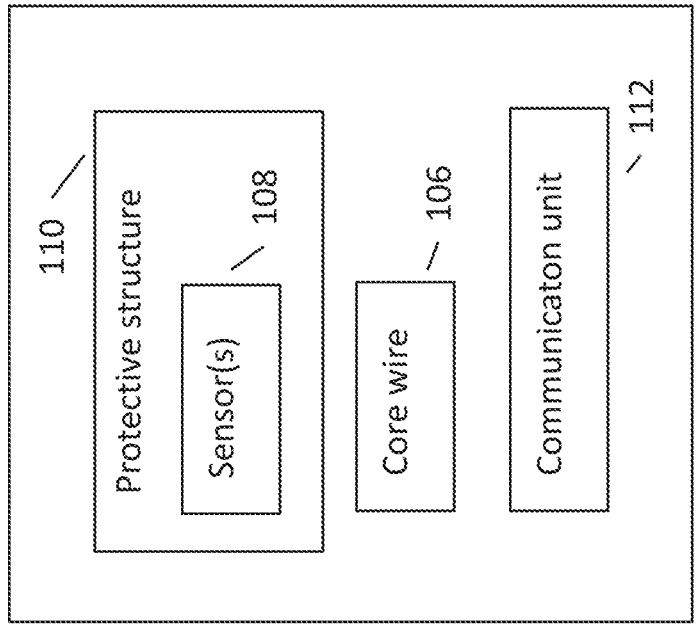

Referring now to FIG. 1, there is shown a block diagram of an exemplary intravascular diagnosis apparatus in accordance with the disclosed technology. The illustrated apparatus 100 includes a monitoring guidewire 102 and a portable display unit 104. In one embodiment, the portable display unit 104 can be a handheld display unit, such that any and all aspects and embodiments described herein as being applicable to a portable display unit are also applicable to the disclosed handheld display unit. In one embodiment, the handheld display unit can be equal to or less than 30 cm×30 cm×30 cm in size. In operation, the monitoring guidewire 102 is introduced into the vasculature of a patient with the assistance of conventional interventional equipment known to those skilled in the art, such as catheters. The portable display unit 104 can communicate with the monitoring guidewire 102 and can display information based on the communications received from the monitoring guidewire 102.

The illustrated monitoring guidewire 102 can include several components, including a core wire 106 and one or more sensors 108 disposed in a distal region of the core wire 106. As used herein, the terms "distal" and "proximal" refer to physical directions within a blood vessel lumen. Specifically, in relation to the insertion point of a device into a patient, the term "distal" refers to the direction from the insertion point inwards into a blood vessel, and the term "proximal" refers to the direction from the inside of a blood vessel out towards the insertion point. As used herein, the terms "proximal" and "distal" can also refer to different ends of a device, with "proximal" being the end towards an insertion point into a blood vessel lumen and with "distal" being the end away from the insertion point.

With continuing reference to FIG. 1, the one or more sensors 108 disposed in a distal region of the core wire 106 can include one or more hemodynamic pressure sensors and/or one or more temperature sensors. In one embodiment, the pressure sensor(s) can be a piezo-resistive pressure sensor. As illustrated in FIG. 1, the monitoring guidewire 102 can also include a protective structure 110 surrounding the sensor(s) 108, and can include a communication unit 112. The protective structure 110 of the monitoring guidewire 102 will be described in more detail later herein in connection with FIGS. 5-6.

In one embodiment, the communication unit 112 can employ wireless communication technology such as bluetooth, WiFi (802.11), or any other wireless technology. In one embodiment, the communication unit 112 can be a wireline communication unit that can include one or more wires for communicating electromagnetic signals and/or one or more optical fibers for communicating optical signals. The monitoring guidewire 102 can include other components that are not illustrated, such as a power source, A/D converters, application specific integrated circuits (ASIC), a processor, memory, timing circuitry, and/or other power, analog, or digital circuitry. Such components will be known to those skilled in the art.

Referring now to the illustrated portable display unit 104, the portable display unit 104 can include a display screen 114, one or more batteries 116, memory and/or storage 118, a communication unit 120, power management unit 122, and a processor 124. In one embodiment, the processor 124 can be a general purpose processor or can be an application specific integrated circuit. In one embodiment, the display screen 114 can be a liquid crystal display, an organic light emitting diode display, or another type of display technology. In one embodiment, the memory/storage 118 can include one or more of solid state memory/storage, magnetic disc storage, and/or any other type of memory/storage that will be known to those skilled in the art. In one embodiment, the memory/storage 118 can include software instructions that are executed by the processor 124. In one embodiment, the communication unit 120 can employ wireless communication technology such as bluetooth, WiFi (802.11), or any other wireless technology. In one embodiment, the communication unit 120 can be a wireline communication unit that can include one or more wires for communicating electromagnetic signals and/or one or more optical fibers for communicating optical signals. The portable display unit 104 can include other components that are not illustrated, such as user interface, operating system software, display driver circuitry, A/D converters, application specific integrated circuits (ASIC), timing circuitry, and/or other power, analog, or digital circuitry. Such components will be known to those skilled in the art.

Figure 2:
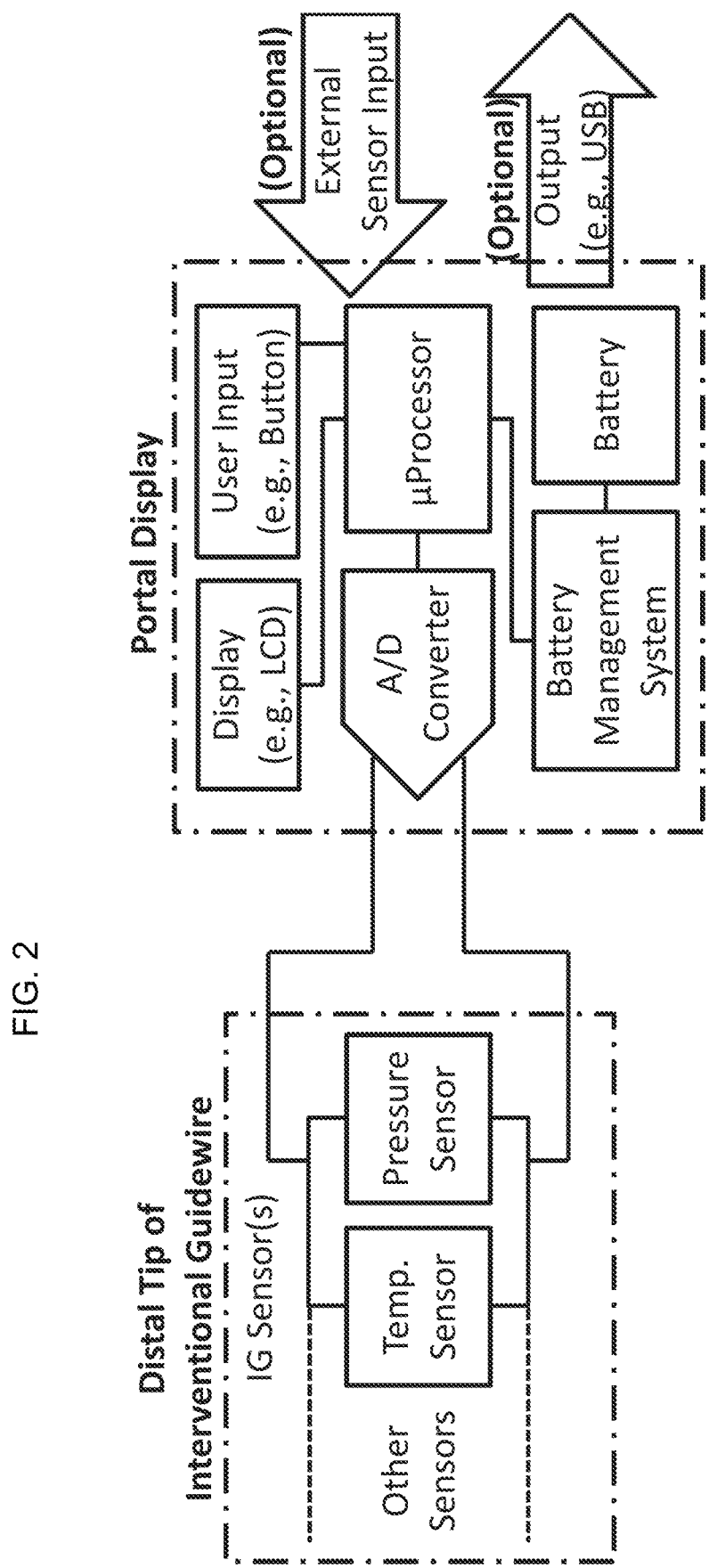
FIG. 2 is a block diagram of an embodiment of the disclosed technology.

Referring now to FIG. 2, there is shown a system block diagram of another embodiment of the disclosed technology. The monitoring guidewire contains a pressure sensor and/or other sensors at the distal end. The electrical signals from the sensor(s) can be sent over a wire connection to the portable display unit. The portable display unit can include a communications port that receives external sensor input such as aortic output pressure (AO IN) from pressure transducers/ hemodynamic systems (not shown). The portable display unit can also include an output communication port for outputting data to an external storage device, to another display, to a printer, and/or to a hemodynamic system (not shown).

Figure 3:
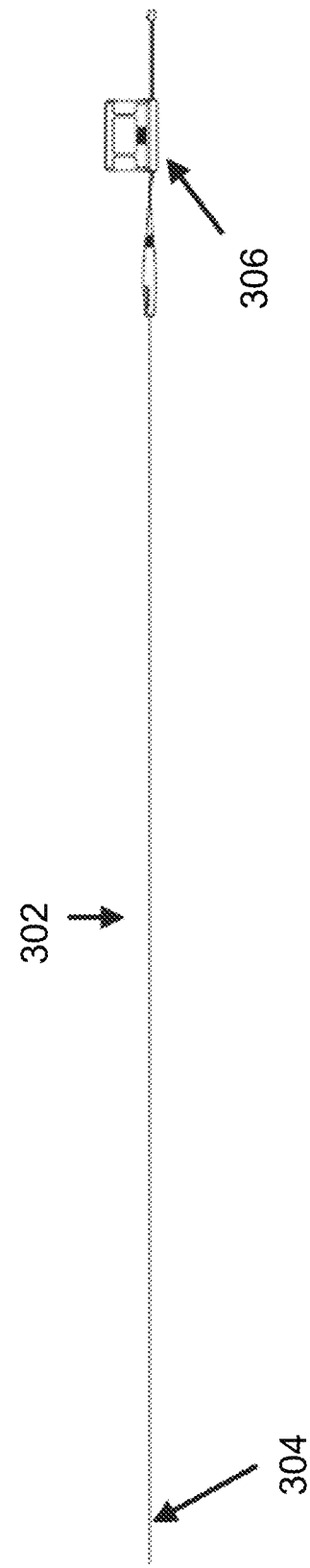
FIG. 3 is a diagram of an exemplary apparatus in accordance with the disclosed technology.

Referring now to FIG. 3, there is shown an exemplary embodiment of the disclosed intravascular diagnosis apparatus. In one embodiment, the monitoring guidewire 302 can be approximately 180 centimeters in length. In other embodiments, the monitoring guidewire 302 can be another length. The monitoring guidewire 302 can have one or more sensors in the distal region 304 of the monitoring guidewire 302. In the illustrated embodiment, the portable display unit 306 can have a small form factor such that it is a handheld display unit. In one embodiment, a handheld display unit can be equal to or less than 30 cm×30 cm×30 cm in size.

Figure 4:
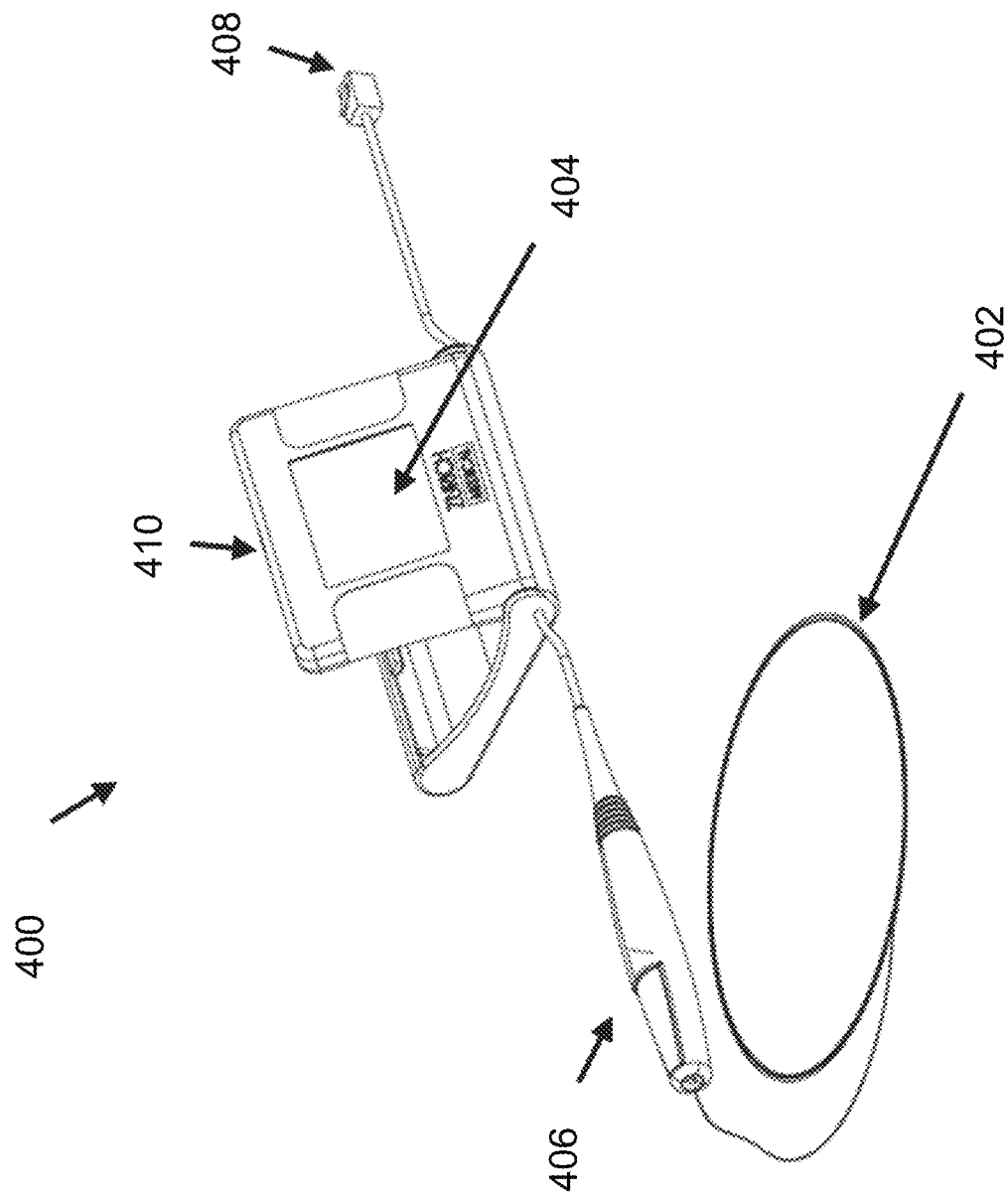
FIG. 4 is another diagram of an exemplary apparatus in accordance with the disclosed technology.

FIG. 4 is a diagram of another exemplary embodiment of the disclosed intravascular diagnosis apparatus. In the illustrated embodiment, the monitoring guidewire 402 can be attached and detached from a connector 406 of the portable display unit 400. In one embodiment, the connector 406 can include a button (not shown) which opens an aperture in the connector 406. To attach or detach the monitoring guidewire 402, a user can press and hold the button of the connector 406 and insert the monitoring guidewire 402 into the aperture until the monitoring guidewire 402 is fully inserted into connector 406. Once inserted, the user can release the button, which will then secure the monitoring guidewire 402 in place and provide a connection between the monitoring guidewire 402 and connector 406. In other embodiments, the connector 406 can engage the monitoring guidewire 402 by a screw engagement, a twist engagement, a snap engagement, or an interference fit. The described types of engagement are exemplary and do not limit the scope of the disclosed technology. Other types of ways for the connector 406 to engage the monitoring guidewire 402 are contemplated to be within the scope of the disclosed technology.

In one embodiment, the connector connection establishes a communicative connection between the monitoring guidewire 402 and the portable display unit 400. The monitoring guidewire 402 and the connector 406 can contain electrical wires that connect the monitoring guidewire 402 to the portable display unit 400 and convey signals from the monitoring guidewire sensor(s) to the portable display unit 400.

In one embodiment, the connector connection establishes a mechanical connection between the monitoring guidewire 402 and the connector 406 to control the guidewire 402 within a vasculature. In the illustrated embodiment, the connector 406 is tethered to the main housing 410 of the portable display unit 400. In one embodiment, the tether can be 6 inches to 12 inches long and can allow a user to manipulate the monitoring guidewire 402 freely without the portable display unit main housing 410 being an impediment. In one embodiment, the tether can be another length. In one embodiment (not shown), the connector can be a connection port integrated in the portable display unit main housing 410.

In one embodiment, the connector 406 establishes a communicative connection with the monitoring guidewire 402. In one embodiment, a torquer (not shown) can be configured to engage the monitoring guidewire 402 to control the guidewire within a vasculature when the monitoring guidewire 402 is not mechanically and/or electrically connected to the connector 406. In one embodiment, the torquer can be configured to engage the monitoring guidewire 402 to control the guidewire within a vasculature when the monitoring guidewire 402 is mechanically and/or electrically connected to the connector 406. In one embodiment, the monitoring guidewire 402 does not need a torquer or the connector 406 for insertion into the vasculature of a patient and for navigation therein, and provides this capability by itself.

With continuing reference to FIG. 4, the portable display unit 400 includes a display screen 404 that can display sensor measurements and/or computed information (e.g., fractional flow reserve ratio), in numerical format and/or in waveform format. The portable display unit 400 can include one or more buttons (not shown) or a touch screen to allow a user to provide input to the portable display unit 400. In one embodiment, the screen 404 of the portable display unit can be folded in the main housing 410 before use to minimize the size of packaging when delivering the portal display unit 400. When a user takes the portable display unit 400 out of the packaging for use, the user can pivot the screen 404 from the folded position to an open position (as illustrated), providing an appropriate viewing angle to the user for the diagnosis procedure. In one embodiment, pivoting of the display screen 404 from the folded position to an open position acts as an ON switch that enables power to be delivered to the portable display unit.

In the illustrated embodiment, the portable display unit 400 also includes a communication port 408. In one embodiment, the communication port 408 allows a user to connect the portable display unit 400 to an external system (not shown). The external system can communicate a sensor signal to the portable display unit 400 through the communication port 408. In one embodiment, the sensor signal received at the communication port can be can be a pressure measurement and can be used in calculating fractional flow reserve.

Figure 5:
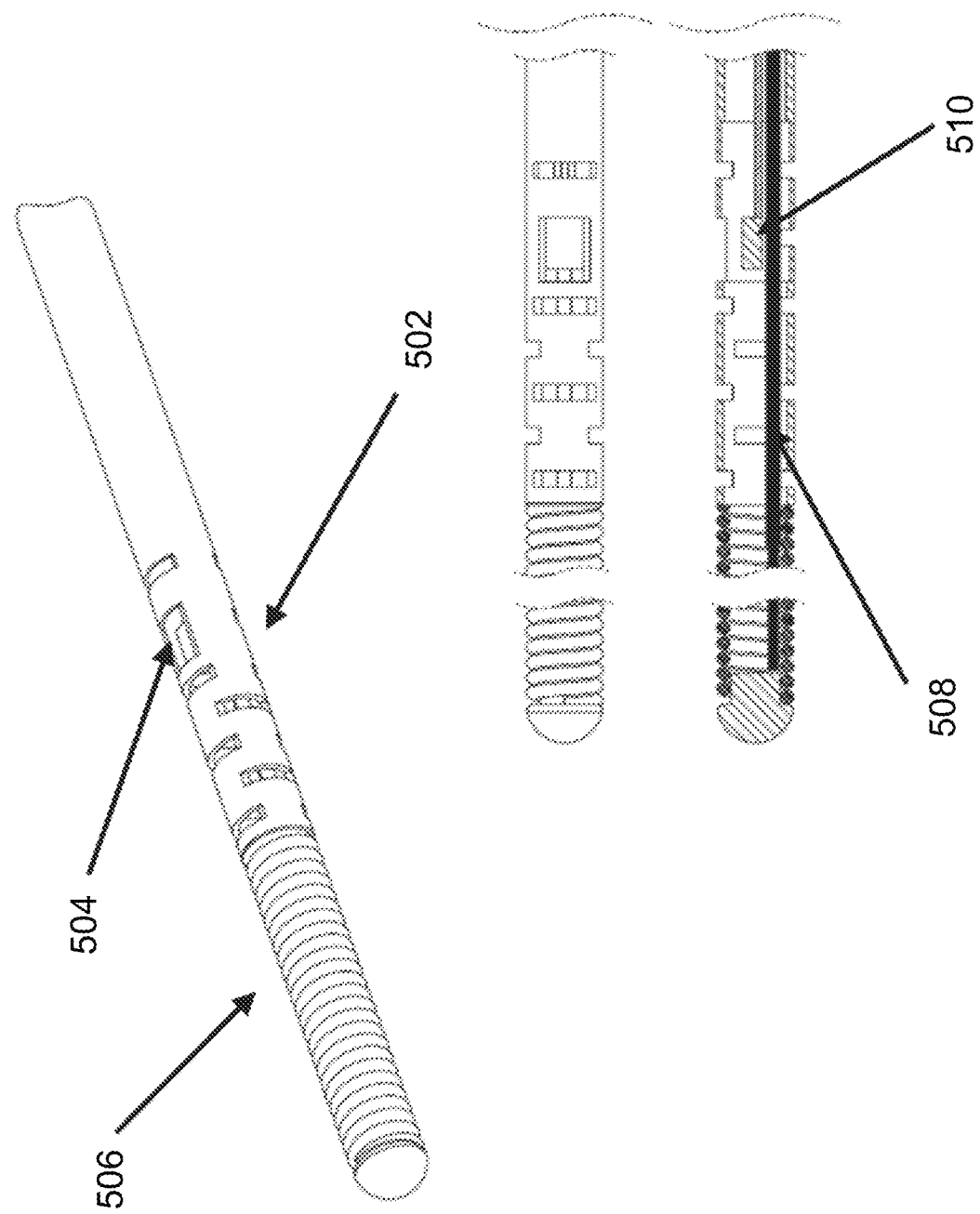
FIG. 5 is a diagram of an exemplary distal tip of the disclosed monitoring guidewire.

Referring again to FIG. 1, the monitoring guidewire 102 can include a protective structure 110 surrounding the sensor(s) 108. With reference to FIG. 5, there is shown a diagram of an exemplary protective structure 502 surrounding the sensor(s) 510 at the distal region of the monitoring guidewire. In the illustrated embodiment, the protective structure 502 is a housing that has been laser etched with a particular pattern cut to provide flexibility and/or torque translation at the distal tip or portion of the monitoring guidewire where the sensor 510 resides. The sensor(s) 510 can be situated in the laser etched housing at a window 504 in the housing so as to allow blood to contact the sensor(s) 510 in order to take sensor measurements. In the illustrated embodiment, the core wire 508 can be grinded to provide an appropriate profile for balancing flexibility and torque translation. In one embodiment, the monitoring guidewire need not include a core wire 508. Rather, the protective structure 502 can extend along the entire monitoring guidewire or a substantial portion thereof, and can be laser etched along some or all portions to provide desired flexibility and/or torque translation.

Figure 6:
FIG. 6 is a diagram of two embodiments of the distal tip of the disclosed monitoring guidewire.

Referring to FIG. 6, there is shown a diagram of two exemplary protective structures surrounding the sensor(s) at the distal region of a monitoring guidewire. One of the embodiments is a laser etched housing as described in connection with FIG. 5. The other embodiment provides a coil over the sensor(s) as the protective structure. The coil is relaxed to create a window where the sensor(s) are located to allow blood to contact the sensor(s). The illustrated embodiments are exemplary and do not limit the scope of protective structures contemplated in the disclosed technology. Other protective structures are contemplated to be within the scope of the disclosed technology.

Various aspects and embodiments of the disclosed technology have been described above. The illustrations and descriptions are merely exemplary and do not limit the scope of the disclosed technology. Even though not illustrated, various embodiments can be combined and are contemplated to fall within the scope of the disclosed technology. Furthermore, although certain features are illustrated as being in a particular location or device, the location and device are merely exemplary, and it is contemplated that various features can be located differently than as illustrated and still be within the scope of the disclosed technology.

The following description will now reference FIG. 1, and in particular, the battery 116 and the power management unit 122 of the portable display unit 104. In one aspect of the disclosed technology, the portable display unit 104 can be configured to operate for a predetermined duration or for a predetermined number of uses, and then be disposed. The battery 116 and/or power management unit 122 can implement these features so that the portable display unit 104 can be inoperable after being used for a particular duration or for a particular number of diagnosis procedures. Even so, the portable display unit 104 can be disposed while it is still operable, prior to it being inoperable.

In one embodiment, the predetermined duration can correspond to the approximate length of time of a single intravascular diagnosis procedure. In one embodiment, the predetermined duration can correspond to the approximate length of time of multiple diagnosis procedures, such as three procedures. In one embodiment, the predetermined duration can be twelve hours or twenty-four hours or several days. In one aspect of the disclosed technology, the portable display unit 104 can include one or more batteries 116 that are configured to power the portable display unit 104 for the desired duration, such that the batteries 116 are substantially depleted at the end of the desired duration. In one embodiment, the one or more batteries 116 are non-rechargeable, so that the portable display unit 104 is disposed after the batteries 116 are depleted. In one embodiment, the power management unit 122 can control the operating time of the portable display unit 104 by preventing the portably display unit 104 from powering down after the display screen 114 is turned on. In such an embodiment, the portable display unit 104 will operate continuously until the batteries 116 are depleted or substantially depleted. The portable display unit 104 can be disposed prior to the batteries 116 being depleted, while the portable display unit 104 is still operable.

In one embodiment, the portable display unit 104 can track the number of diagnosis procedures performed and can be configured to be inoperable after a particular number of procedures has been performed. In one embodiment, the portable display unit 104 can track the number of diagnosis procedures performed by the number of times the portable display unit 114 has been turned on and/or off. In one embodiment, the portable display unit 104 can be configured to be inoperable after a single diagnosis procedure has been performed. In one aspect of the disclosed technology, the power management unit 122 can prevent the portable display unit 104 from being powered on after the particular number of procedures has been reached. The batteries 116 can be rechargeable and can be recharged by a power source of the portable display unit 104 and/or by a power source external to the portable display unit 104. Even when the batteries 116 are not yet depleted, the power management unit 122 can cause the portable display unit 104 to be inoperable by preventing the batteries 116 from powering the portable display unit 104.

The intravascular diagnosis procedure will now be described with continuing reference to FIG. 1 and with reference to FIGS. 7-11. Diagnosing the severity of one or more stenoses within the vasculature of a patient has been studied based on hemodynamic pressure measurements distal to a stenosis in comparison with aortic output pressure. The ratio of pressure distal to a stenosis to the aortic output pressure is known as "factional flow reserve", or FFR. The value of the FFR indicates the severity of the stenosis, and clinical data provides guidance on the type of surgical procedure that would be effective for particular FFR ranges.

The disclosed technology includes multiple ways of computing FFR, including what will be referred to herein as "push-forward FFR", "pull-back FFR", and "simultaneous FFR". Each of these can be implemented by software code or machine code stored in memory/storage 118 of the portable display unit 104 (FIG. 1). The processor 124 can execute the software code to compute the FFR, and the resulting information can be displayed on the display screen 114. Each of the computation methods will now be described.

Simultaneous Fraction Flow Reserve

Figure 9:
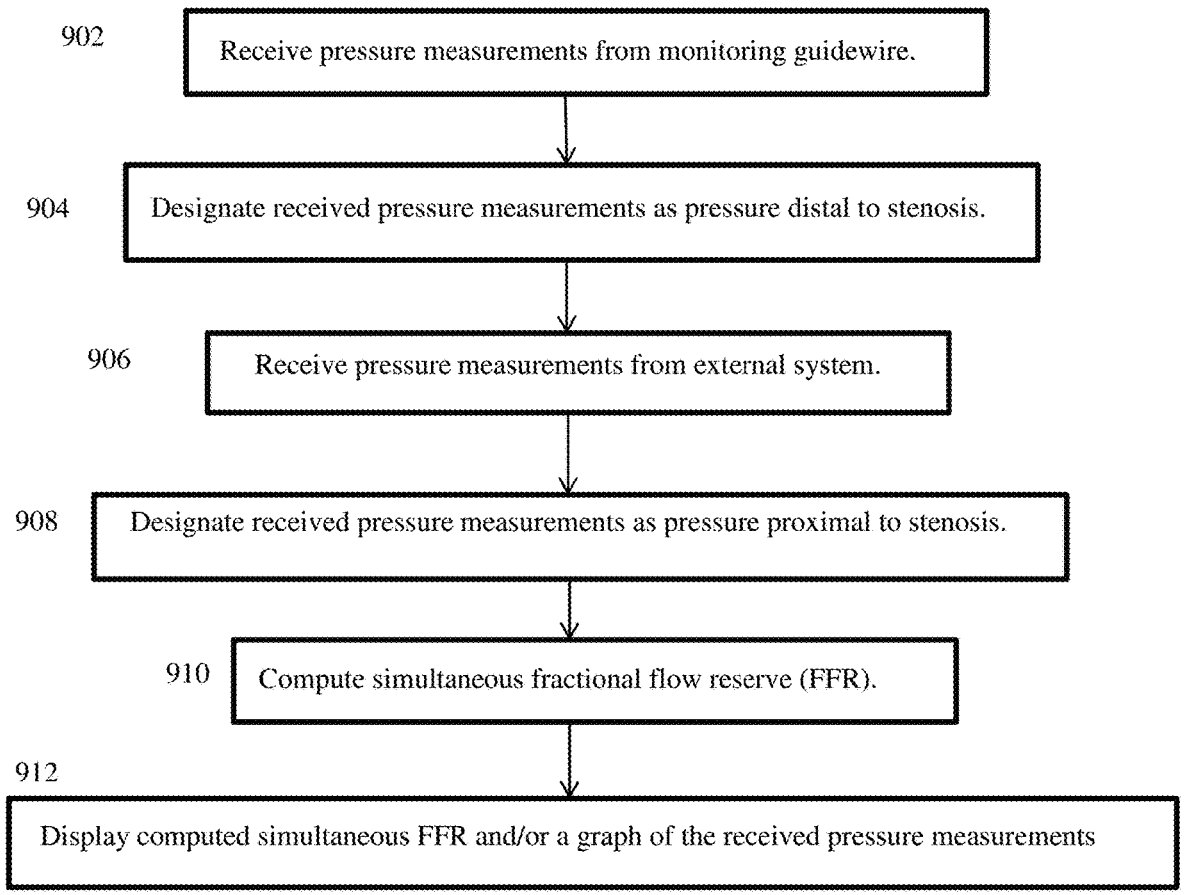
FIG. 9 is a flow diagram of exemplary operation of the disclosed technology for computing simultaneous fractional flow reserve.
Figure 10:
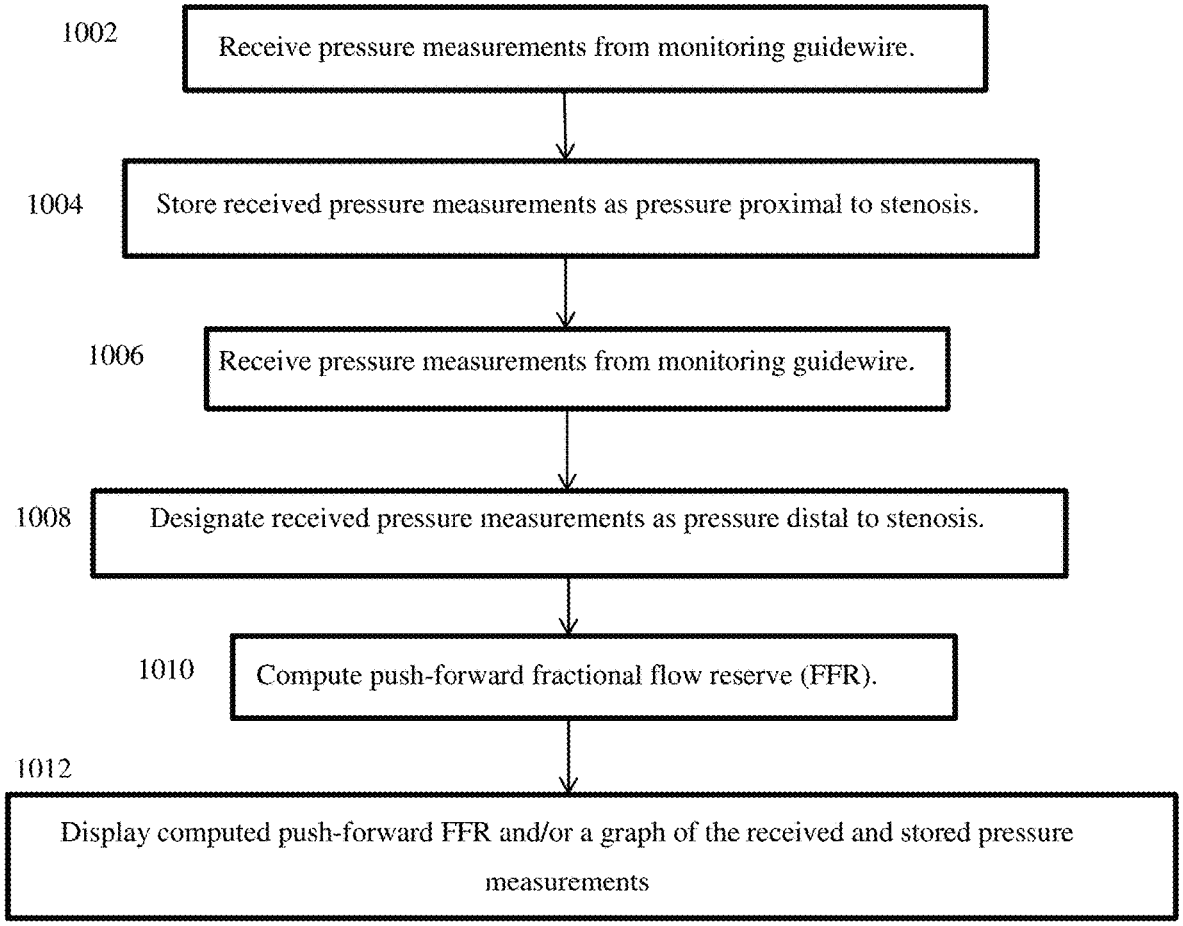
FIG. 10 is a flow diagram of exemplary operation of the disclosed technology for computing push-forward fractional flow reserve.
Figure 11:
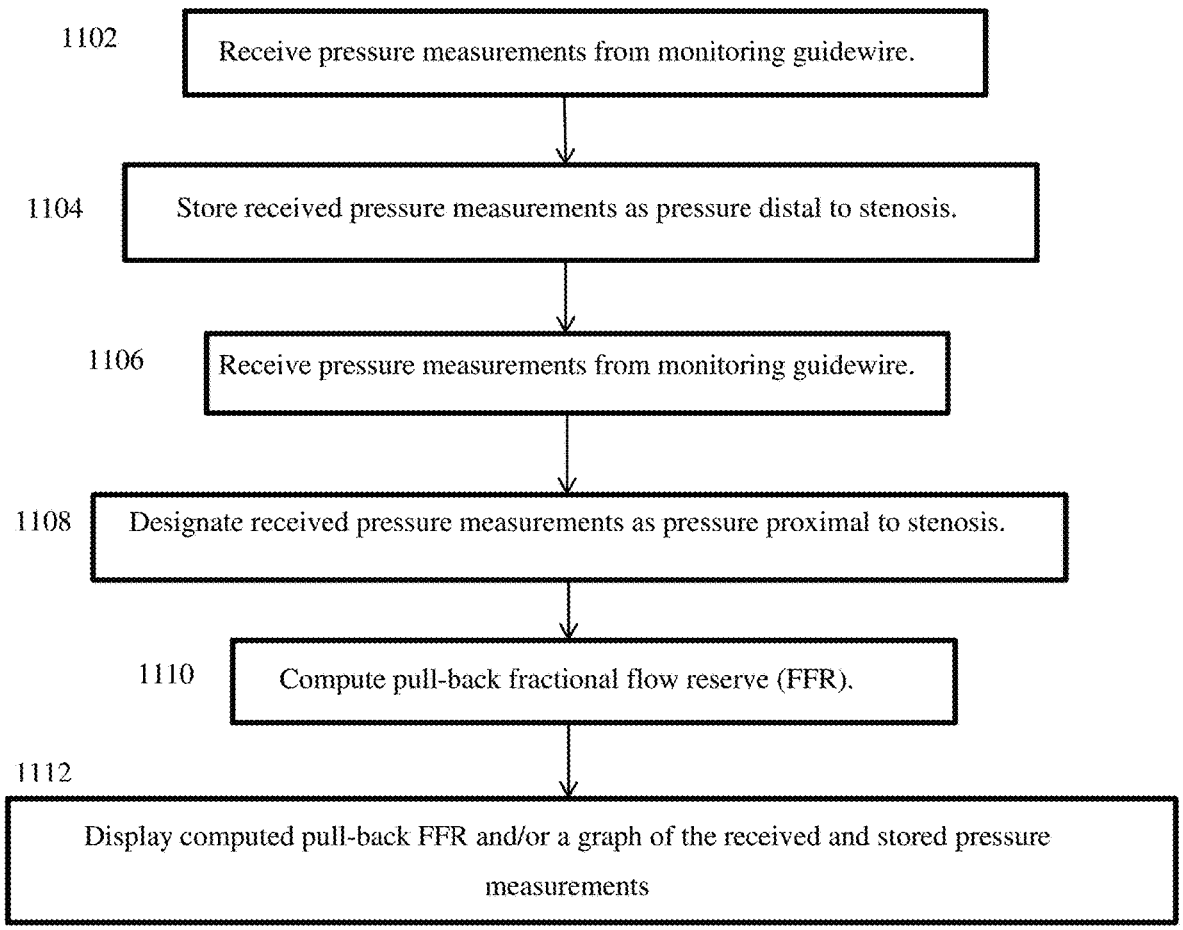
FIG. 11 is a flow diagram of exemplary operation of the disclosed technology for computing pull-back fractional flow reserve.

Simultaneous FFR involves simultaneous pressure readings from two separate pressure sensors, and a computation of FFR in real-time as the pressure readings from the two separate pressure sensors are received. Referring to FIG. 1 and FIG. 9, one pressure sensor is located in the monitoring guidewire 102, and is used to measure pressure distal to a stenosis in a patient. The pressure readings can be communicated by the communication unit 112 of the monitoring guidewire 102 to the communication unit 120 of the portable display unit 104 (902). This communication can be a wireless communication or can be a wireline communication through, for example, the connector illustrated in FIG. 3. The other pressure sensor can measure aortic output pressure and is external to the apparatus 100 of FIG. 1. The portable display unit 104 can designate the received pressure measurements as pressure distal to a stenosis (904). The external sensor readings can be communicated to the communication unit 120 of the portable display unit by, for example, the communication port illustrated in FIG. 3 (906). The portable display unit 104 can designate the received pressure measurements as pressure proximal to a stenosis (908). The portable display unit 104 can compute the simultaneous FFR as the pressure measurements are received (910), by the formula: $FFR=(P_{sensor}-P_{ra})/(P_{port}-P_{ra})$, where:

$P_{port}$ are moving means over time of real-time pressure measurements received at the communications port, $P_{sensor}$ are moving means over time of real-time pressure measurements from the pressure sensor in the distal region of the core wire of the monitoring guidewire, and $P_{ra}$ is a constant, which can be zero or another constant value.

In one embodiment, the moving means over time can compute the mean over a window of time that spans one heartbeat. In other embodiments, the window of time can span less than one heartbeat or more than one heartbeat. As new sensor measurements are received over time (902, 906), the window can include newer measurements and remove older measurements to compute the moving means.

The portable display unit 104 can receive pressure measurements and can compute the simultaneous FFR based on the received measurements. The portable display unit 104 can store the received pressure measurements and/or the computed simultaneous FFR in memory/storage 118, and can display the computed simultaneous FFR and/or a graph of the received pressure measurements on the display screen 114 (912).

Push-Forward Fractional Flow Reserve

Figure 7:
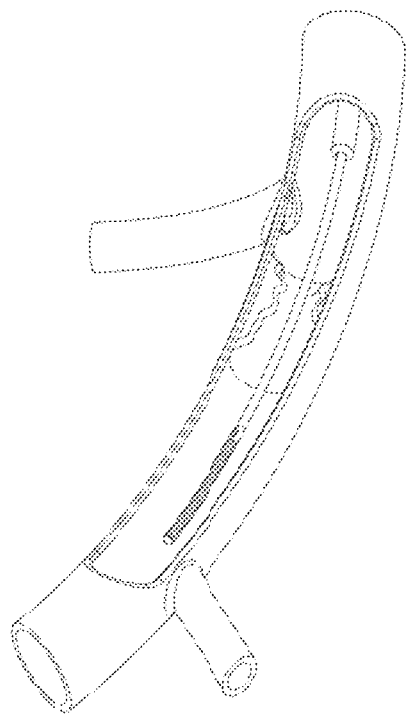
FIG. 7 is a diagram of one position for the disclosed monitoring guidewire for estimating fractional flow reserve.
Figure 8:
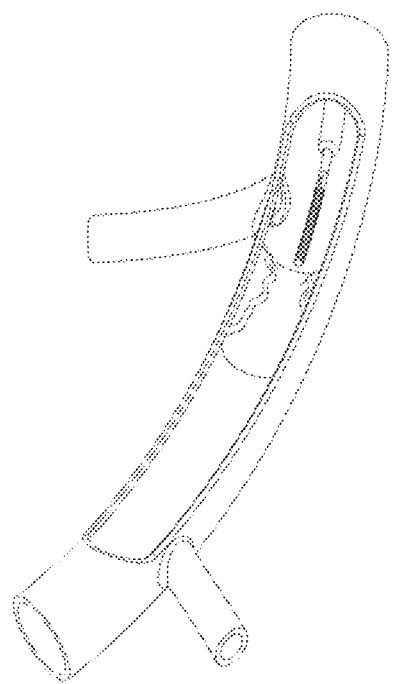
FIG. 8 is a diagram of another position for the disclosed monitoring guidewire for estimating fractional flow reserve.

In contrast to simultaneous FFR, the push-forward FFR does not receive external pressure measurements. With continuing reference to FIG. 1, push-forward FFR is computed using pressure measurements from only the pressure sensor(s) 108 in the distal region of the monitoring guidewire 102. Using traditional angiography, a stenosis can be located and, as shown in FIG. 8, the monitoring guidewire can be inserted into a patient to a point proximal to the stenosis. Pressure can be measured at this position by the sensor(s) 108 and communicated by the communication unit 112 to the portable display unit 104 (1002). The portable display unit 104 can store the measurements in this position in the memory/storage 118 as pressure proximal to a stenosis (1004). Next, the monitoring guidewire 102 can be pushed forward past the stenosis to a point distal to the stenosis, as illustrated in FIG. 7. Pressure can be measured at this position by the sensor(s) 108 and communicated by the communication unit 112 to the portable display unit 104 (1006). The portal display unit 104 can designate the pressure measurements received at this position as pressure distal to the stenosis (1008). The processor 124 can compute the push-forward FFR (1010) by the formula: $FFR=(P_{sensor}-P_{ra})/(P_{saved}-P_{ra})$, where:

$P_{saved}$ are moving means over time of recorded pressure measurements proximal to the stenosis, $P_{sensor}$ are moving means over time of real time pressure measurements distal to the stenosis, and $P_{ra}$ is a constant, which can be zero or another constant value.

Aspects of computing the moving means over time were described above in connection with simultaneous FFR, and such aspects apply to push-forward FFR as well.

The portal display unit 104 can display the computed push-forward FFR and/or a graph of the received and stored pressure measurements (1012).

Push-forward FFR can be computed in the case of one stenosis and can also be computed in the case of multiple stenosis. In either case, $P_{saved}$ are moving means over time of pressure measurements proximal to all of the stenosis. In one embodiment, $P_{saved}$ are moving means over time computed based on recorded pressure measurements. In one embodiment, $P_{saved}$ are moving means over time computed and recorded as pressure measurements are received, and the pressure measurements may or may not be recorded. For example, in the case of two stenoses, $P_{saved}$ are based on pressure measurements proximal to both the first and second stenosis. When the monitoring guidewire pressure sensor 108 is pushed forward to a position between the first and the second stenosis, $P_{sensor}$ are based on real time pressure measurements between the two stenoses. Push-forward FFR can be calculated in this position and displayed on the display screen 114. When the monitoring guidewire pressure sensor 108 is pushed forward to a position distal to both the first and second stenoses, $P_{sensor}$ are based on real time pressure measurements distal to both of the two stenoses. Push-forward FFR can be calculated in this position and displayed on the display screen 114. Thus, push-forward FFR enables FFR to be computed and displayed as the monitoring guidewire 102 is pushed forward across one or more stenoses in a blood vessel lumen. The only measurements and/or moving means that need to be recorded for push-forward FFR computations are pressure measurements and/or moving means of pressure measurements proximal to all stenoses, and this is performed at the outset.

Pull-Back Fractional Flow Reserve

Similar to push-forward FFR, the pull-back FFR does not receive external pressure measurements. Rather, pull-back FFR is computed using pressure measurements from only the pressure sensor(s) 108 in the distal region of the monitoring guidewire 102. Using traditional angiography, a stenosis can be located and, as shown in FIG. 7, the monitoring guidewire can be inserted into a patient to a point distal to the stenosis. Pressure can be measured at this position by the sensor(s) 108 and communicated by the communication unit 112 to the portable display unit 104 (1102). The portable display unit 104 can store the measurements in this position in the memory/storage 118 as pressure distal to a stenosis (1104). Next, the monitoring guidewire 102 can be pulled back through the stenosis to a point proximal to the stenosis, as illustrated in FIG. 8. Pressure can be measured at this position by the sensor(s) 108 and communicated by the communication unit 112 to the portable display unit 104 (1106). The portable display unit 104 can designate the measurements received in this position as pressure proximal to a stenosis (1108). The processor 124 can compute the pull-back FFR (1110) by the formula:

$$FFR = (P_{saved} - P_{ra})/(P_{sensor} - P_{ra})$$

where:

$P_{saved}$ are moving means over time of recorded pressure measurements distal to the stenosis, $P_{sensor}$ are moving means over time of real time pressure measurements proximal to the stenosis, and $P_{ra}$ is a constant, which can be zero or another constant value.

Aspects of computing the moving means over time were described above in connection with simultaneous FFR, and such aspects apply to pull-back FFR as well.

The portal display unit 104 can display the computed pull-back FFR and/or a graph of the received and stored pressure measurements (1112).

Pull-back FFR can be computed in the case of one stenosis and can also be computed in the case of multiple stenosis. In either case, $P_{sensor}$ are based on real-time pressure measurements proximal to all of the stenosis, which are the final pressure measurements that are taken. For example, in the case of two stenoses, the monitoring guidewire pressure sensor 108 is initially placed at a position distal to both the first and the second stenoses. Pressure can be measured at this position by the sensor(s) 108 and communicated by the communication unit 112 to the portable display unit 104. In one embodiment, $P_{saved\_d1}$ are moving means over time computed later based on recorded pressure measurements. In one embodiment, $P_{saved\_d1}$ are moving means over time computed and recorded while the pressure measurements are received in this position, and the pressure measurements may or may not be recorded. The memory/storage 118 can record the pressure measurements in this position and/or computed moving means over time based on such pressure measurements. Pull-back FFR cannot yet be calculated because there is no real-time measurement yet proximal to all of the stenoses. Next, the monitoring guidewire 102 can be pulled back through the first stenosis to a point between the first and second stenosis. Pressure can be measured at this position by the sensor(s) 108 and communicated by the communication unit 112 to the portable display unit 104. In one embodiment, $P_{saved\_d2}$ are moving means over time computed later based on recorded pressure measurements. In one embodiment, $P_{saved\_d1}$ are moving means over time computed and recorded while the pressure measurements are received in this position, and the pressure measurements may or may not be recorded. The memory/storage 118 can record the pressure measurements in this position and/or computed moving means over time based on such pressure measurements. Once again, pull-back FFR cannot yet be calculated because there is no real-time measurement yet proximal to all of the stenoses. Lastly, the monitoring guidewire 102 can be pulled back through the second stenosis to a point proximal to both the first and second stenosis. Real-time pressure can be measured at this position by the sensor(s) 108 and communicated by the communication unit 112 to the portable display unit 104. Only at this point are there enough measurements to compute the two pull-back FFR: $FFR_1 = (P_{saved\_d1} - P_{ra})/(P_{sensor} - P_{ra})$ and $FFR_2 = (P_{saved\_d2} - P_{ra})/(P_{sensor} - P_{ra})$. Therefore, pull-back FFR does not allow FFR to be calculated and displayed as the monitoring guidewire is being pulled back through multiple stenoses.

Accordingly, three computations for fractional flow reserve have been described above in connection with FIGS. 7-11. In one aspect of the disclosed technology, and with reference to FIG. 1, the portable display unit 104 is configured with capability to compute fractional flow reserve using any of the three ways. In one embodiment, the portable display unit 104 can be configured to automatically use one of the three ways of computing fractional flow reserve. In one embodiment, the portable display unit 104 can be configured to automatically select one of the three ways of computing fractional flow reserve when a condition is present and to automatically select another of the three ways of computing fractional flow reserve when other conditions are present. In one embodiment, the portable display unit 104 can be configured to permit a user to manually select one of the three ways of computing fraction flow reserve.

The disclosed technology measures pressure and calculates fractional flow reserve (FFR). FFR is a calculation that has been clinically demonstrated to assist in determining whether to treat or not to treat an intermediate coronary lesion. Using the disclosed technology will thus assist a physician in determining what to do with an intermediate lesion. The disclosed FFR equations are exemplary and do not limit the scope of the disclosed technology. Other ways to compute FFR are contemplated to be within the scope of the disclosed technology.

The illustrations, embodiments, and specifications disclosed herein are exemplary and do not limit the spirit and scope of the disclosed technology. Combinations of one or more disclosed embodiments or specification, or portions of one or more embodiments or specifications, are contemplated as being within the scope of the disclosed technology.

What is claimed is:

1. A portable display device for displaying fractional flow reserve information, the portable display device comprising:
   a housing;
   a display screen in the housing in a folded position before use, wherein pivoting the display screen from the folded position to an open position acts as an ON switch, wherein the portable display device has no capability of being turned off after the display screen is pivoted to the open position; and
   a processor within the housing, the processor configured to perform fractional flow reserve computations based on sensor measurements and to cause the display screen to display fractional flow reserve information based on the fractional flow reserve computations.

2. The portable display device of claim 1, further comprising at least one non-rechargeable battery within the housing,
   wherein after the display screen is pivoted to the open position, the at least one non-rechargeable battery operates continuously until it is depleted based on the portable display device having no capability of being turned off after the display screen is pivoted to the open position.

3. The portable display device of claim 1, further comprising a connector configured to be attachable to and detachable from a guidewire, the connector configured to establish a communicative connection with the guidewire when the guidewire is attached to the connector.

4. The portable display device of claim 1, further comprising a wireless receiver configured to wirelessly receive the sensor measurements from a guidewire.

5. The portable display device of claim 1, wherein the sensor measurements are pressure measurements.

6. The portable display device of claim 5, wherein the fraction flow reserve computations are computed based on:
recorded pressure measurements proximal to a first stenosis, and
distal pressure measurements distal to the first stenosis, the distal pressure measurements being measured after the recorded pressure measurements are recorded.

7. The portable display device of claim 6, wherein the distal pressure measurements are measured distal to the first stenosis and proximal to a second stenosis.

8. The portable display device of claim 6, wherein:
the recorded pressure measurements are measured proximal to the first stenosis and proximal to a second stenosis, and
the distal pressure measurements are measured distal to the first stenosis and distal to the second stenosis.

9. The portable display device of claim 5, wherein the fraction flow reserve is computed based on:
recorded pressure measurements distal to a first stenosis, and
proximal pressure measurements proximal to the first stenosis, the proximal pressure measurements being measured after the recorded pressure measurements are recorded.

10. The portable display device of claim 9, wherein the proximal pressure measurements are measured proximal to the first stenosis and distal to a second stenosis.

11. The portable display device of claim 9, wherein:
the recorded pressure measurements are measured distal to the first stenosis and distal to a second stenosis, and
the proximal pressure measurements are measured proximal to the first stenosis and proximal to the second stenosis.

12. The portable display device of claim 1, further comprising a communications port configured to receive communications that include pressure measurements.

13. The portable display device of claim 12, wherein the processor is configured to perform the fractional flow reserve computations further based on the pressure measurements received at the communications port.

14. The portable display device of claim 12, wherein the processor is capable of performing the fractional flow reserve computations in at least two ways comprising: performing the fractional flow reserve computations based on only the sensor measurements, and performing the fractional flow reserve computations based on the sensor measurements and based on pressure measurements received at the communications port.

15. The portable display device of claim 14, wherein the processor is configured to receive a user selection of one of the at least two ways of performing the fraction flow reserve computations.

16. A handheld display device for displaying fractional flow reserve information, the handheld display device comprising:
a housing configured to be handheld;
a display screen in the housing in a folded position before use, wherein pivoting the display screen from the folded position to an open position acts as an ON switch, wherein the handheld display device has no capability of being turned off after the display screen is pivoted to the open position; and
a processor within the housing, the processor configured to perform fractional flow reserve computations based on sensor measurements and to cause the display screen to display fractional flow reserve information based on the fractional flow reserve computations.

17. The handheld display device of claim 16, wherein the housing has a length equal to or less than 30 cm, a width equal to or less than 30 cm, and a depth equal to or less than 30 cm.

18. A portable display device comprising:
a housing;
a display screen in the housing in a folded position before use, wherein pivoting the display screen from the folded position to an open position acts as an ON switch, wherein the portable display device has no capability of being turned off after the display screen is pivoted to the open position; and
a processor within the housing, the processor configured to perform computations based on sensor measurements from a guidewire and to cause the display screen to display information based on the computations.

* * * * *